United States Patent
Carlson et al.

(10) Patent No.: US 9,140,662 B1
(45) Date of Patent: Sep. 22, 2015

(54) PREVENTING STRAY CURRENTS IN SENSORS IN CONDUCTIVE MEDIA

(71) Applicant: Honeywell International Inc., Morristown, NJ (US)

(72) Inventors: Robert Jon Carlson, Brooklyn Park, MN (US); Thomas E. Nohava, Apple Valley, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/463,087

(22) Filed: Aug. 19, 2014

(51) Int. Cl.
| | |
|---|---|
| *G01N 27/333* | (2006.01) |
| *G01N 27/414* | (2006.01) |
| *H01L 29/06* | (2006.01) |
| *H01L 29/66* | (2006.01) |

(52) U.S. Cl.
CPC .......... *G01N 27/414* (2013.01); *H01L 29/0653* (2013.01); *H01L 29/66553* (2013.01)

(58) Field of Classification Search
CPC ................................................. G01N 27/4165
See application file for complete search history.

(56) References Cited

U.S. PATENT DOCUMENTS

| | | | | |
|---|---|---|---|---|
| 4,961,833 A | * | 10/1990 | Sakai et al. | 257/253 |
| 5,944,970 A | * | 8/1999 | Rosenblatt | 204/416 |
| 7,939,932 B2 | | 5/2011 | Martin | |
| 2005/0050944 A1 | * | 3/2005 | Ha et al. | 73/53.01 |
| 2007/0250142 A1 | | 10/2007 | Francis et al. | |
| 2008/0124889 A1 | * | 5/2008 | Roggenbauer et al. | 438/404 |
| 2011/0027128 A1 | | 2/2011 | Gridelet et al. | |
| 2013/0158378 A1 | | 6/2013 | Berger et al. | |
| 2013/0302932 A1 | | 11/2013 | Bustillo et al. | |
| 2014/0106494 A1 | * | 4/2014 | Bedell et al. | 438/49 |
| 2014/0145709 A1 | | 5/2014 | O'Riordan et al. | |

OTHER PUBLICATIONS

Kim et al., "PH Sensing and Noise Characteristics of Si Nanowire Ion-Sensitive Field Effect Transistors", "Proceedings of the 2011 6th IEEE International Conference of Nano/Micro Engineered and Molecular Systems", Feb. 20, 2011, pp. 1233-1236, Publisher: IEEE, Published in: TW.

Prodromakis et al., "Exploiting CMOS Technology to Enhance the Performance of ISFET Sensors", "IEEE Electron Device Letters", Aug. 25, 2010, pp. 1053-1055, vol. 31, No. 9, Publisher: IEEE, Published in: US.

Reddy Jr. et al., "High-K Dielectric Al2O3 Nanowire and Nanoplate Field Effect Sensors for Improved PH Sensing", "NIH Public Access", Apr. 2011, pp. 1-18, Publisher: National Institutes of Health, Published in: US.

* cited by examiner

*Primary Examiner* — Angel Roman
(74) *Attorney, Agent, or Firm* — Fogg & Powers LLC

(57) ABSTRACT

A sensor is provided. The sensor includes a conductive substrate having side-walls; a dielectric layer overlaying a first surface of the conductive substrate, the dielectric layer including a gate dielectric having a first thickness and a field dielectric having a second thickness; a sensing layer overlaying a first surface of the gate dielectric; a non-conductive carrier wherein a second surface of the conductive substrate overlays a portion of the non-conductive carrier; and an insulating layer conformally coating at least the side-walls of the conductive substrate, wherein a first surface of the sensing layer is uncoated by the insulating layer.

20 Claims, 4 Drawing Sheets

PREVENTING STRAY CURRENTS IN SENSORS IN CONDUCTIVE MEDIA

BACKGROUND

When sensors and integrated circuits are immersed in a conductive fluid, unwanted electrical current can flow, disrupting the operation of the device. For example, a pH sensor and circuit are immersed in a conductive fluid (seawater). The device's sidewalls of the sensor are exposed and un-passivated due to the die separation step (sawing for example). Electrical current can then flow from the exposed sidewalls into the sensor's circuit.

Currently available pH sensors use O-rings or epoxy to seal the conductive fluid from the sidewalls. However, pH sensors for use in the ocean at depths much greater than a kilometer have failures. Specifically, the high pressure of the ocean at depth causes the O-rings or epoxy to fail. This type of failure is exacerbated by repeated pressure cycling. The failure of the O-rings or epoxy allows conductive fluid leaks and current flow from the unpassivated exposed sidewall of the device.

SUMMARY

Sensors that are immune to stray currents and method of making sensors that are immune to stray currents are described herein and will be understood by reading and studying the following specification. The present application relates to a sensor. The sensor includes a conductive substrate having side-walls; a dielectric layer overlaying a first surface of the conductive substrate, the dielectric layer including a gate dielectric having a first thickness and a field dielectric having a second thickness; a sensing layer overlaying a first surface of the gate dielectric; a non-conductive carrier wherein a second surface of the conductive substrate overlays a portion of the non-conductive carrier; and an insulating layer conformally coating at least the side-walls of the conductive substrate, wherein a first surface of the sensing layer is uncoated by the insulating layer.

DRAWINGS

Figure 1:
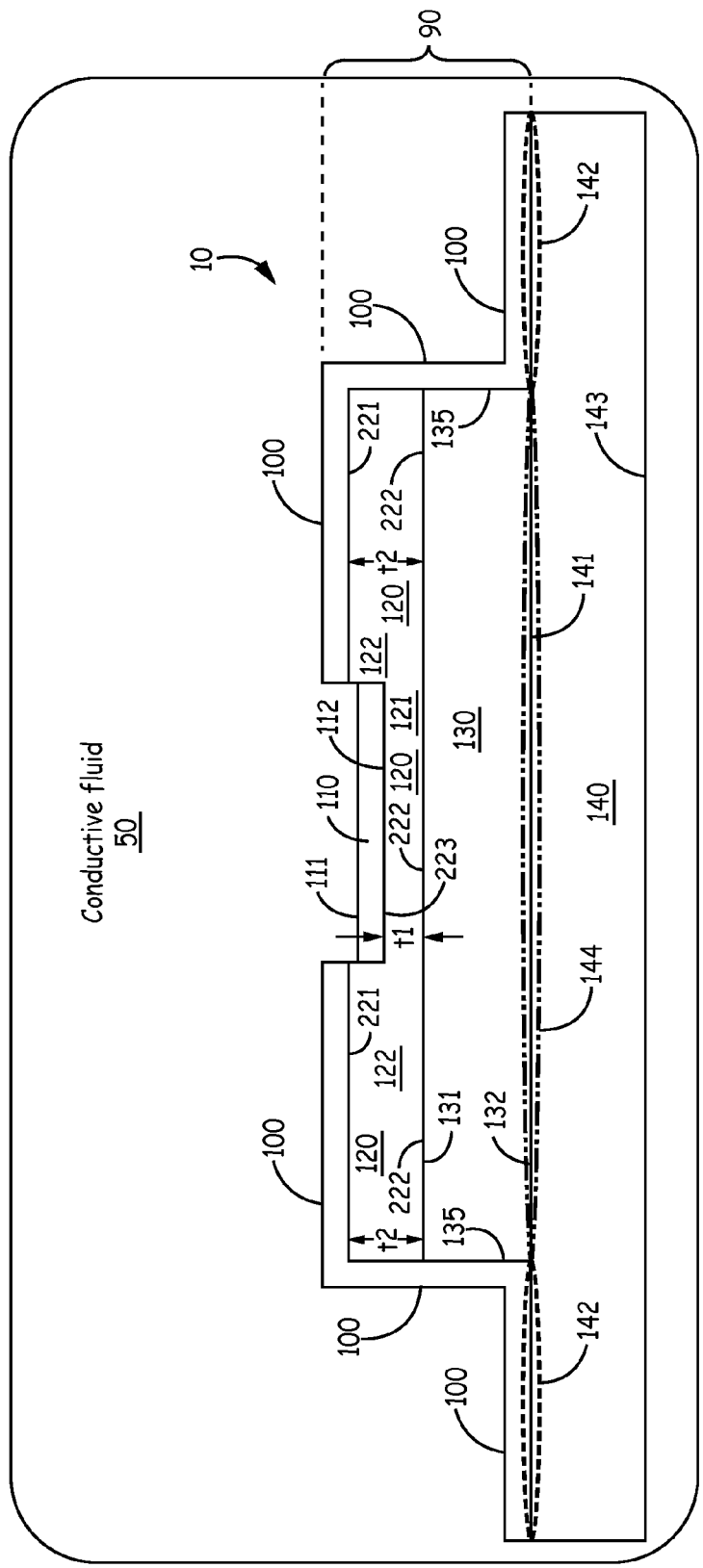
Figure 2:
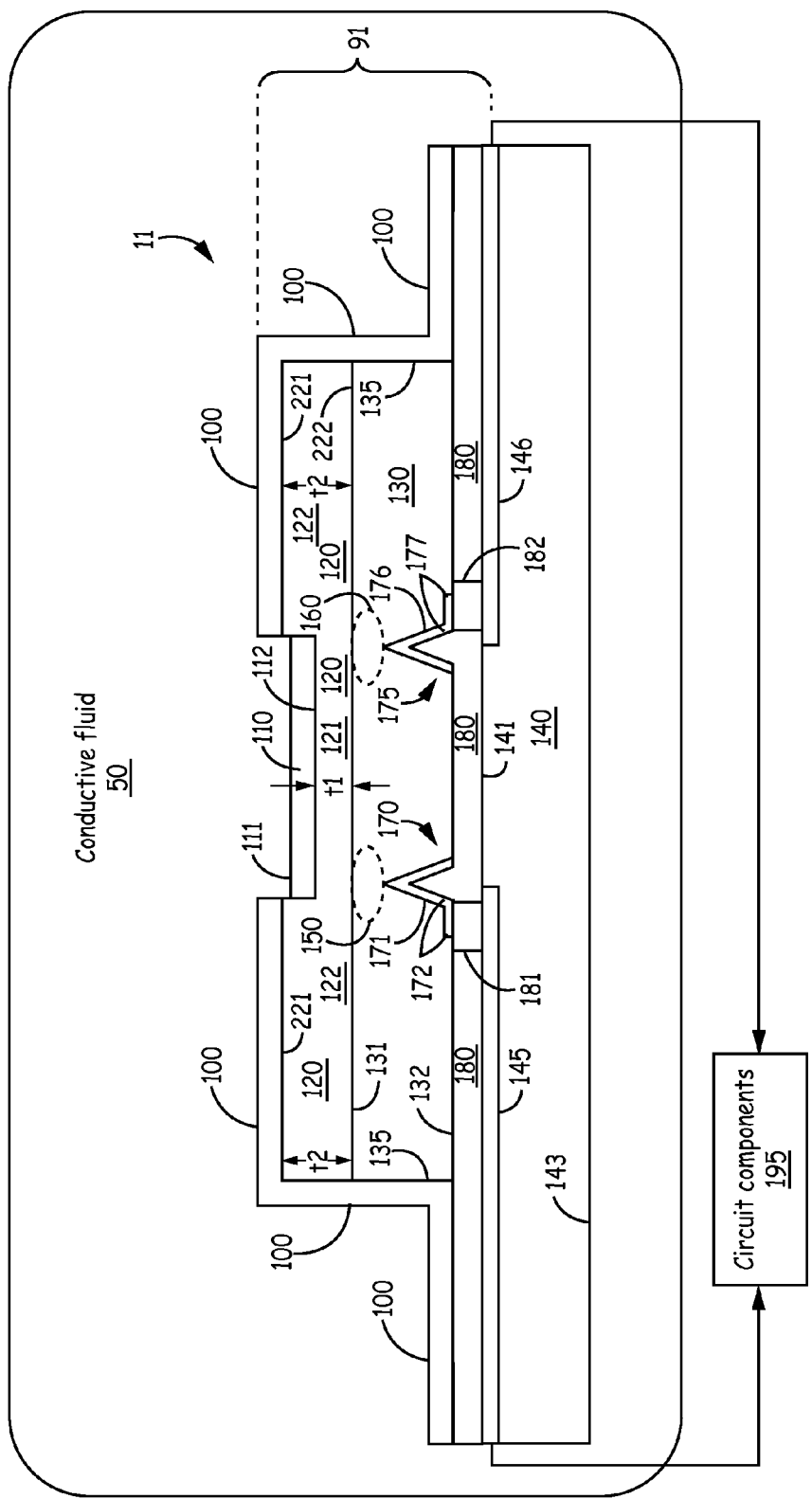
Figure 3:
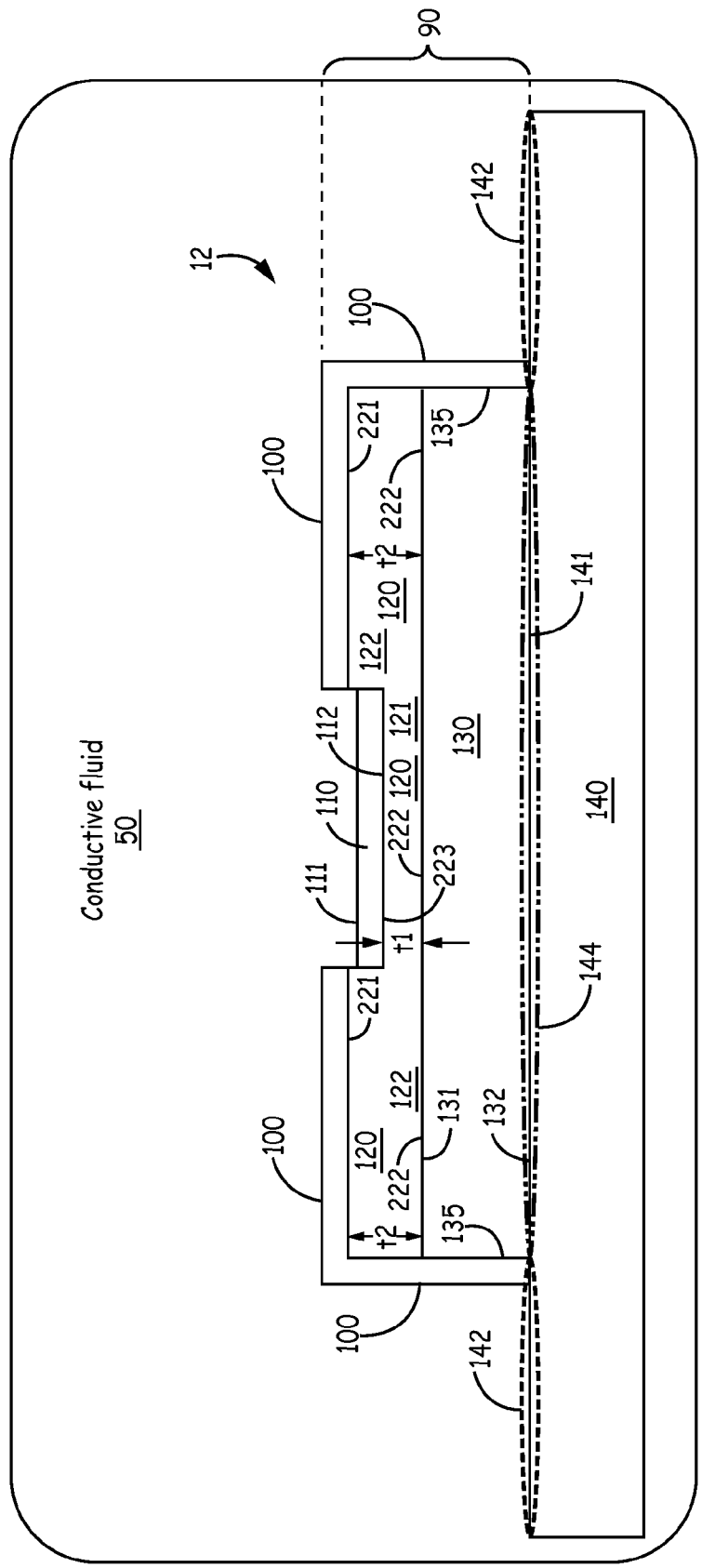
Figure 4:
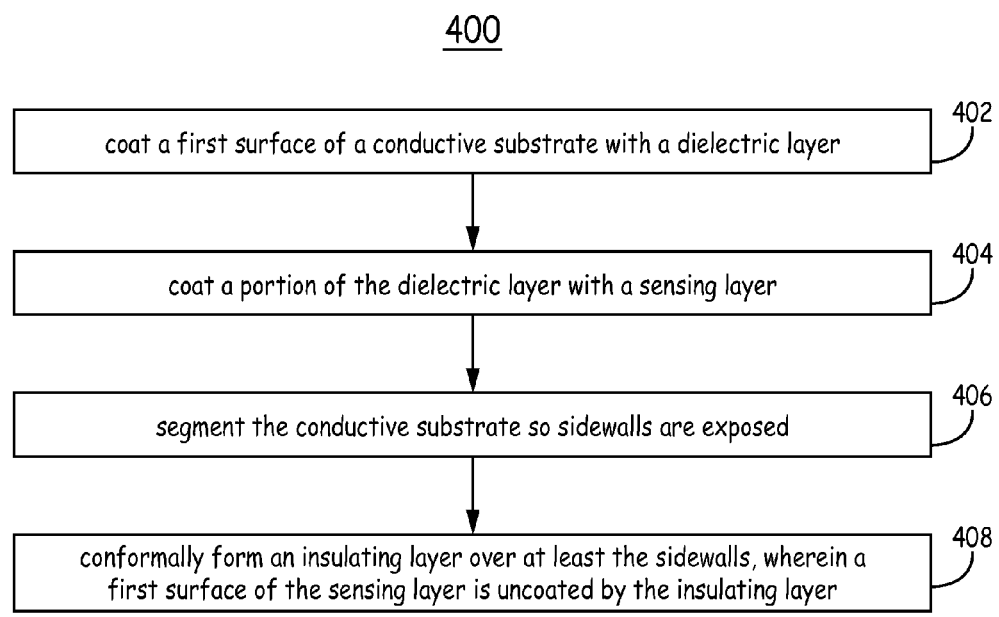

Embodiments of the present application can be more easily understood and further advantages and uses thereof more readily apparent, when considered in view of the description of the embodiments and the following figures in which:

FIGS. 1-3 show embodiments of sensors that are immune to stray currents in accordance with the present application; and FIG. 4 is a flow diagram of a method of fabricating sensors that are immune to stray currents in accordance with the present application.

In accordance with common practice, the various described features are not drawn to scale but are drawn to emphasize features relevant to the present invention. Reference characters denote like elements throughout figures and text.

DETAILED DESCRIPTION

In the following detailed description, reference is made to the accompanying drawings that form a part hereof, and in which is shown by way of specific illustrative embodiments in which the sensors may be implemented. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Embodiments of the sensors described herein are protected from stray currents and do not fail under high pressure or under repeated pressure cycling (e.g., from high pressure to low pressure to high pressure, and so on).

FIGS. 1-3 show embodiments of sensors that are immune to stray currents in accordance with the present application. FIG. 1 shows a cross-sectional view of the structure of the layers of a sensor 10. Sensor 10 includes a sensor chip 90 and a non-conductive carrier 140. The sensor chip 90 includes a conductive substrate 130, a dielectric layer 120, a sensing layer 110, and an insulating layer 100. The non-conductive carrier 140 is a chip carrier 140. The circuitry used to obtain measurements from the sensor 10 is not shown in FIG. 1.

The non-conductive carrier 140 has a first surface 141 and an opposing second surface 143. The conductive substrate 130 has a first surface 131, an opposing second surface 132, and side-walls 135. The sidewalls 135 are also referred to herein as "sidewall surfaces 135". The conductive substrate 130 overlays a portion 144 of the surface 141 of the non-conductive carrier 140. The second surface 132 of the conductive substrate 130 contacts the portion 144 of the first surface 141 of the non-conductive carrier 140. The dielectric layer 120 overlays the conductive substrate 130. The second surface 222 of the dielectric layer 120 contacts the first surface 131 of the conductive substrate 130.

The dielectric layer 120 includes a gate dielectric 121 having a first thickness $t_1$ and a field dielectric 122 having a second thickness $t_2$. The field dielectric 122 has a first surface 221 and an opposing second surface 222. The gate dielectric 121 has a first surface 223 and an opposing second surface 222. As shown in FIG. 1, the gate dielectric 121 and the field dielectric 122 are formed contiguously in the dielectric layer 120 and they share the second surface 222. Since the second thickness $t_2$ is greater than the first thickness $t_1$, the gate dielectric 121 is surrounded by the field dielectric 122.

The sensing layer 110 has first surface 111 and an opposing second surface 112. The sensing layer 110 overlays the first surface 223 of the gate dielectric 121. The second surface 112 of the sensing layer 110 contacts the first surface 223 of the gate dielectric 121.

The insulating layer 100 conformally coats at least the side-walls 135 of the conductive substrate 130. The first surface 111 of the sensing layer 110 is uncoated by the insulating layer 100. As shown in FIG. 1, the insulating layer 100 conformally coats: 1) the side-walls 135 of the conductive substrate 130; 2) the first surface 221 of the field dielectric 122; and 3) an exposed surface 142 of the non-conductive carrier 140. The exposed surface 142 of the non-conductive carrier 140 is defined as that portion of the surface 141 of the non-conductive carrier 140 that is not overlaid by the conductive substrate 130 of the sensor chip 90.

In one implementation of this embodiment, the conformal coatings are formed by vapor based chemical reactions, which are repeatedly cycled to deposit an atomic layer with each deposition cycle. The insulating layer 100 deposited in this manner is a high quality dielectric that contiguously and evenly deposits material on all exposed surfaces, even vertical surfaces. The insulating layer 100 is also referred to herein as "atomic-layer-deposition layer 100", an "ALD layer 100", and "ALD 100".

In one implementation of this embodiment, the insulating layer 100 is deposited using Atomic Layer Deposition (ALD). In another implementation of this embodiment, the insulating layer 100 is deposited using one of the types of chemical vapor deposition (CVD). In yet another implementation of this embodiment, the insulating layer 100 is approximately or less than 1000 Angstroms.

The first surface 111 of the sensing layer 110 is the surface that is exposed to the environment to be sensed. As shown in FIG. 1, the first surface 111 of the sensing layer 110 is the surface that is exposed to a conductive fluid 50.

In one implementation of this embodiment, the sensor 10 is a pH sensor 10 used to measure the pH of a liquid (e.g., conductive fluid 50). The dielectric layer 120 and sensing layer 110 are operable to sense pH when exposed to the conductive fluid 50. When pH sensors are used in high pressures situations (e.g., deep in the ocean) or in repeated pressure cycling situations, the pH sensors are known to cause bending of the non-conductive carrier.

In prior art pH sensors that use an O-ring to insulate the sidewalls from the conductive fluid, the bending of the non-conductive carrier under high pressure and/or repeated pressure cycling causes the O-ring to pop off of the device so the sidewalls are exposed. Similarly, in prior art pH sensors that use epoxy to insulate the sidewalls from the conductive fluid, the bending of the non-conductive carrier under high pressure and/or repeated pressure cycling causes the epoxy to delaminate from the sides walls so the sidewalls are exposed to the fluid being sensed. In both cases, a desired current flows from the sidewall to the sensing surface and the prior art pH sensors have erroneous measurements.

Because the ALD layer 100 of the sensor 10 has high integrity and good adhesion to the sidewalls 135, the ALD layer 100 is able to withstand high pressure and repeated pressure cycling without cracking or shifting away from the sidewall 134. Even when the non-conductive carrier 140 bends under the pressure, the thin atomic layers of the ALD layer 100 of the sensor 10 remain adhered to the sidewalls 135. Thus, no undesired stray currents are generated to flow between the sidewalls 135 and the first surface 111 of the sensing layer via the conductive fluid 50 and the sensor 10 accurately measures the pH of the conductive fluid 50.

In one implementation of this embodiment, the insulating layer 100 conformally coats the side-walls 135 of the conductive substrate 130 but does not coat the entire first surface 221 of the field dielectric 122. In another implementation of this embodiment, the conductive substrate 130 is a silicon substrate. In another implementation of this embodiment, the conductive substrate 130 is a p doped silicon substrate. In yet another implementation of this embodiment, the non-conductive carrier 140 is formed from a plastic material as known to one skilled in the art.

FIG. 2 shows a layer structure of a sensor 11 with circuit components 195. Sensor 11 is similar to sensor 10 in that it includes a non-conductive carrier 140 and a sensor chip 91. The sensor chip 91 includes a conductive substrate 130, a dielectric layer 120 including the gate dielectric 121 and the field dielectric 122, a sensing layer 110, and an insulating layer 100 (ALD 100). The sensor 11 also includes a first electrode 145 inlaid in the non-conductive carrier 140, a second electrode 146 inlaid in the non-conductive carrier 140, a first via 170 in the conductive substrate 130, and a second via 175 in the conductive substrate 130, and an insulating layer 180. The first via 170 and the second via 175 are electrically conductive.

A first conductive material 181 that extends through the insulating layer 180 is formed in the insulating layer 180. In one implementation of this embodiment, the first conductive material 181 is formed by etching a through hole in the insulating layer 180 and filling the through hole with a metal or metal alloy. A second conductive material 182 that extends through the insulating layer 180 is formed in the insulating layer 180. In one implementation of this embodiment, the second conductive material 182 is formed by etching a second through hole in the insulating layer 180 and filling the second through hole with a metal or metal alloy. The first and second conductive material 181 and 182 are also referred to herein as respective first and second conductive pads 181 and 182.

The first via 170 electrically connects a source diffusion region represented generally at 150 to the first electrode 145 via the first conductive pad 181 in the insulating layer 180. The second via 175 electrically connects a drain diffusion region represented generally at 160 to the second electrode 146 via the second conductive pad 182 in the insulating layer 180. The circuit components 195, when electrically connected to the first electrode 145 and the second electrode 146 as shown in FIG. 2, are operable to sense a current generated within the sensor 11 based on the environment of the sensing layer 110, e.g., the conductive fluid 50. The circuit components 195 are shown in FIG. 2 to be external to the conductive fluid 50. However, in embodiments, the circuit components 195 are packaged with the sensor 11 and the package is in the conductive fluid 50. In one implementation of this embodiment, there is no insulating layer 180.

In one implementation of this embodiment, the insulating layer 180 is formed from silicon oxide. In this case, the insulating layer 180 is a silicon dioxide layer 180. In another implementation of this embodiment, the conductive substrate 130 is a silicon substrate with appropriate p-n junction layers to form the desired channel. In yet another implementation of this embodiment, the first via 170 is formed by etching a first cavity 171 in the conductive substrate 130 and coating the inner surface of the first cavity 171 with a conductive material 172. In one implementation of this embodiment, the conductive material 172 is a metal or metal alloy (for example, gold). The conductive material 172 electrically contacts the first conductive pad 181 in the insulating layer 180. In yet another implementation of this embodiment, the second via 175 is formed by etching a second cavity 176 in the conductive substrate 130 and coating the inner surface of the second cavity 176 with a conductive material 177. In one implementation of this embodiment, the conductive material 177 is a metal or metal alloy (for example, gold). The conductive material 177 electrically contacts the second conductive pad 182 in the insulating layer 180.

The sensor 11 is operable as a pH sensor 11. The pH of a conductive fluid 50 is a function of the number of hydrogen ions in the conductive fluid 50 as is known to one skilled in the art. The material in the sensing layer 110 (e.g., gate 110) absorbs hydrogen ions (protons) from the conductive fluid 50. When hydrogen ions interact with the sensing layer 110, the sensor chip 91 in the sensor 11 is operable as a field effect transistor (FET) 91, in which the sensing layer 110 functions as a gate 110 and the conductive substrate 130 functions as a channel. As the gate 110 is charged up by the interacting hydrogen ions in the conductive fluid 50, the current flow in the channel 130 increases. The current is measured between the source diffusion region 150 and the drain diffusion region 160.

As is understandable to one skilled in the art upon reading and understanding this document, the sensor 10 of FIG. 1 can be implemented with the first electrode 145, the second electrode 146, the first via 170 in the conductive substrate 130, the second via 175 in the conductive substrate 130 and the insulating layer 180 as shown in FIG. 2.

FIG. 3 shows a layer structure of a sensor 12. The layer structure of sensor 12 differs from the sensor 11 of FIG. 3 in that the ALD 100 does not cover the exposed surface 142 of the non-conductive carrier 140 that is not overlaid by the conductive substrate 130. In this embodiment, the ALD 100 is deposited on the sensor chip 90 formed by the conductive substrate 130, the dielectric layer 120, and the sensing layer 110 before the sensor chip 90 is placed on the non-conductive carrier 140. For the embodiment of the sensor 10 shown in FIG. 1, the sensor chip 90 is placed on the non-conductive carrier 140 and then the ALD 100 is deposited on the sensor chip 90 and the non-conductive carrier 140.

As is understandable to one skilled in the art upon reading and understanding this document, the sensor 12 can be implemented with the first electrode 145, the second electrode 146, the first via 170 in the conductive substrate 130, the second via 175 in the conductive substrate 130 and the insulating layer 180 as described above with reference to FIG. 2.

FIG. 4 is a flow diagram of a method 400 of fabricating sensors that are immune to stray currents in accordance with the present application. The method 400 is described with reference to the sensors 10, 11, and 12 of respective FIGS. 1, 2, and 3. However, it is to be understood, that method 400 is applicable to adaptations or variations of the sensors shown and described herein.

At block 402, a first surface 131 of a conductive substrate 130 is coated with a dielectric layer 120. The dielectric layer 120 can be deposited using one or more of a variety of techniques for deposition known to one skilled in the art. In one implementation of this embodiment, the dielectric layer 120 is deposited with a second thickness $t_2$ and a portion of the dielectric layer 120 is etched to form a gate dielectric 121 with a first thickness $t_1$ in the field dielectric 122. In this case, the first thickness $t_1$ is less than the second thickness $t_2$. In another implementation of this embodiment, a first via 170 and a second via 175 are formed in the conductive substrate 130 (FIG. 2). In yet another implementation of this embodiment, the first via 170 is formed by etching a first cavity 171 and coating the inner surface of the first cavity with a conductive material 172 while ensuring that the conductive material 172 is isolated from the conductive substrate 130 as is understandable to one skilled in the art. In yet another implementation of this embodiment, the second via 175 is formed by etching a second cavity 176 and coating the inner surface of the second cavity 176 with a conductive material 177 while ensuring that the conductive material 177 is isolated from the conductive substrate 130 as is understandable to one skilled in the art.

At block 404, a portion (e.g., the gate dielectric 121) of the dielectric layer 120 is coated with a sensing layer 110. The sensing layer 110 can be deposited using one or more of a variety of techniques for deposition known to one skilled in the art. In one implementation of this embodiment, the sensing layer 110 is formed from metal oxides as known to one skilled in the art. The sensing layer 110 is deposited on the portion of the dielectric layer 120 that was etched back to form the gate dielectric 121 with a first thickness $t_1$. In one implementation of this embodiment, the first thickness $t_1$ of the gate dielectric 121 in combination with the thickness of the sensing layer 110 are less than the second thickness $t_2$ of the field dielectric 122. In this case, the first surface 111 of the sensing layer 110 is closer to the first surface 131 of the conductive substrate 130 than the first surface 221 of the field dielectric 122.

At block 406, the conductive substrate 130 is segmented to form sensor chips and sidewalls 135 of the conductive substrate 130 are exposed due to the segmenting. In one implementation of this embodiment, the segmenting process is done by sawing the substrate (wafer) into a plurality of sensor chips 90. In another implementation of this embodiment, the segmenting process is done by notching the substrate and cleaving the substrate to break along the crystalline planes due to the notches.

At block 408, an insulating layer 100 is conformally formed over at least the sidewalls 135 of the conductive substrate 130 that was exposed by the segmenting at block 406. The first surface 111 of the sensing layer 110 is uncoated by the insulating layer 100. In this manner, after die separation exposes the sidewalls 135 and after the sensor chip 90 or 91 is attached to a header (e.g., non-conductive carrier 140), the conformal insulating layer 100 coats the entire sensor 10, 11, or 12 to eliminate any conductive path through the conductive fluid 50 between the first surface 111 of the sensing layer 110 and the sidewalls 135.

The insulating layer 100 is conformally formed in vapor based chemical reaction used to deposit a dielectric onto the exposed sidewall surfaces of the conductive substrate 130. In particular, Atomic Layer Deposition (ALD) and other forms of chemical vapor deposition (CVD) are able to deposit a high quality dielectric on all exposed surfaces, even vertical surfaces. Because the ALD has high integrity and good adhesion, it withstands high pressure and pressure cycling. A processing step is needed to make clear the first surface 111 of the sensing layer 110 of the ALD.

Often the sensing material of the sensing layer 110 is fragile and can be damaged when the ALD 100 is removed from the first surface 111 of the sensing layer 110. This damage can be prevented by depositing and patterning a sacrificial layer on the sensing layer 110 before the ALD 100 is deposited to protect the material of the sensing layer 110. The sacrificial layer is removed later. For example, the first surface 111 of the sensing layer 110 is protected from the insulating layer by a deposition of a protective sacrificial material (e.g., aluminum) on the first surface 111 of the sensing layer 110 prior to the deposition of the conformal insulating layer 100 on the sidewalls 135 of the conductive substrate. Then the protective material (e.g., aluminum) protecting the first surface 111 of the sensing layer 110 and the insulating layer 100 conformally formed over the protective material is lifted off of the first surface 111 of the sensing layer 110 so the first surface 111 of the sensing layer 110 is exposed to the environment.

In one implementation of this embodiment, the conductive substrate 130 of the sensor chip 90 or 91 is positioned on a non-conductive carrier 140 prior to step 408 so that the non-conductive carrier 140 is also conformally coated with the insulating layer 100. This embodiment is shown in the sensor 10 of FIG. 1.

In another implementation of this embodiment, the conductive substrate 130 of the sensor chip 90 or 91 is positioned on a non-conductive carrier 140 after step 408 so that the non-conductive carrier 140 is not conformally coated with the insulating layer 100. This embodiment is shown in the sensor 12 of FIG. 3.

In yet another implementation of this embodiment, a first electrode 145 and a second electrode 146 are formed in the non-conductive carrier 140 along with any required trace lines to communicatively couple the first electrode 145 and the second electrode 146 to circuit components 195 (FIG. 2). In this case, an insulating layer 180 is formed between the non-conductive carrier 140 and the second surface 132 of the conductive substrate 130. This ensures the first electrode 145 and the second electrode 146 are electrically isolated from the conductive substrate 130 except for the points of contact between the first via 170 and the first electrode 145 and between the second via 175 and the second electrode 146 when the sensor chip 90 or 91 is positioned on the non-conductive carrier 140. In one embodiment, the insulating layer 180 is a layer of silicon dioxide 180 formed between the non-conductive carrier 140 and a second surface 132 of the conductive substrate 130. In another implementation of this embodiment, the insulating layer 180 is an oxide layer.

Example Embodiments

Example 1 includes a sensor comprising: a conductive substrate having side-walls; a dielectric layer overlaying a first surface of the conductive substrate, the dielectric layer including a gate dielectric having a first thickness and a field dielectric having a second thickness; a sensing layer overlaying a first surface of the gate dielectric; a non-conductive carrier wherein a second surface of the conductive substrate overlays a portion of the non-conductive carrier; and an insulating layer conformally coating at least the side-walls of the conductive substrate, wherein a first surface of the sensing layer is uncoated by the insulating layer.

Example 2 includes the sensor of Example 1, wherein the insulating layer is an atomic layer having a thickness less than 1000 Angstroms.

Example 3 includes the sensor of any of Examples 1-2, wherein the insulating layer conformally coats the field dielectric.

Example 4 includes the sensor of any of Examples 1-3, wherein the insulating layer conformally coats the field dielectric, and an exposed surface of the non-conductive carrier.

Example 5 includes the sensor of any of Examples 1-4, further comprising: circuit components, wherein the dielectric layer, the sensing layer, and the circuit components are operable to sense pH of a conductive fluid when the sensing layer is exposed to the conductive fluid.

Example 6 includes the sensor of any of Examples 1-5, further comprising: a first electrode; a second electrode; a first via formed in the conductive substrate, the first via electrically connecting a source diffusion region to the first electrode; and a second via formed in the conductive substrate, the second via electrically connecting a drain diffusion region to the second electrode, wherein, when the sensor is operable, the sensing layer functions as a gate, and the conductive substrate functions as a channel.

Example 7 includes the sensor of Example 6, further comprising: a layer of silicon dioxide formed between the non-conductive carrier and the second surface of the conductive substrate, the layer of silicon dioxide overlaying the first electrode and the second electrode.

Example 8 includes the sensor of any of Examples 1-7, wherein the conductive substrate is a silicon substrate.

Example 9 includes the sensor of any of Examples 1-8, wherein the conductive substrate is a p doped silicon substrate.

Example 10 includes the sensor of any of Examples 1-9, wherein the dielectric layer and sensing layer sense pH when exposed to a conductive fluid.

Example 11 includes a method of forming a sensor that is immune to stray currents, comprising coating a first surface of a conductive substrate with a dielectric layer; coating a portion of the dielectric layer with a sensing layer; segmenting the conductive substrate, wherein sidewalls are exposed; and conformally forming an insulating layer over at least the sidewalls, wherein a first surface of the sensing layer is uncoated by the insulating layer.

Example 12 includes the method of Example 11, further comprising: positioning the conductive substrate on a non-conductive carrier.

Example 13 includes the method of any of Examples 11-12, further comprising: positioning the conductive substrate on a non-conductive carrier prior to conformally forming the insulating layer over at least the sidewalls, wherein the insulating layer overlays a portion of a surface of the non-conductive carrier.

Example 14 includes the method of any of Examples 11-13, further comprising; etching a portion of the dielectric layer, wherein coating the portion of the dielectric layer with the sensing layer includes: coating the etched portion of the dielectric layer with the sensing layer.

Example 15 includes the method of any of Examples 11-14, further comprising: forming a first electrode in a non-conductive carrier; forming a second electrode in the non-conductive carrier; forming a first via in the conductive substrate; forming a second via in the conductive substrate; and positioning the conductive substrate on a non-conductive carrier.

Example 16 includes the method of Example 15, further comprising: forming an insulating layer between the non-conductive carrier and a second surface of the conductive substrate, the insulating layer overlaying the first electrode and the second electrode; forming a first conductive material in the insulating layer; and forming a second conductive material in the insulating layer.

Example 17 includes the method of any of Examples 15-16, further comprising: forming a layer of silicon dioxide between the non-conductive carrier and a second surface of the conductive substrate, the layer of silicon dioxide overlaying the first electrode and the second electrode; forming a first conductive pad in the layer of silicon dioxide; and forming a second conductive pad in the layer of silicon dioxide.

Example 18 includes the method of any of Examples 15-17, wherein forming the first via in the conductive substrate comprises: etching a first cavity in the conductive substrate; and coating an inner surface of the first cavity with a metal or a metal alloy, and wherein forming the first via in the conductive substrate comprises: etching a second cavity in the conductive substrate; and coating an inner surface of the second cavity with the metal or the metal alloy.

Example 19 includes a pH sensor comprising: a non-conductive carrier; a first electrode inlaid in the non-conductive carrier; a second electrode inlaid in the non-conductive carrier; a conductive substrate having a first surface, a second surface, and side-walls, the conductive substrate overlaying at least a portion of the non-conductive carrier; a dielectric layer overlaying the first surface of the conductive substrate, the dielectric layer including a gate dielectric having a first thickness and a field dielectric having a second thickness; a sensing layer overlaying a first surface of the gate dielectric; an insulating layer conformally coating at least the side-walls of the conductive substrate, wherein a first surface of the sensing layer is uncoated by the insulating layer; a first via formed in the conductive substrate, the first via electrically connecting a source diffusion to the first electrode; and a second via formed in the conductive substrate, the second via electrically connecting a drain diffusion to the second electrode, wherein, when the pH sensor is operable, the sensing layer functions as a gate, and the conductive substrate functions a channel.

Example 20 includes the pH sensor of Example 19, further comprising: a layer of oxide formed between the non-conductive carrier and the second surface of the conductive substrate overlaying the first electrode and the second electrode; a first conductive pad extending through the layer of oxide; and a second conductive pad extending through the layer of oxide.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A sensor comprising:
   a conductive substrate having side-walls;
   a dielectric layer overlaying a first surface of the conductive substrate, the dielectric layer including a gate dielectric having a first thickness and a field dielectric having a second thickness;
   a sensing layer overlaying a first surface of the gate dielectric;
   a non-conductive carrier wherein a second surface of the conductive substrate overlays a portion of the non-conductive carrier; and
   an insulating layer conformally coating at least the sidewalls of the conductive substrate, wherein a first surface of the sensing layer is uncoated by the insulating layer.

2. The sensor of claim 1, wherein the insulating layer is an atomic layer having a thickness less than 1000 Angstroms.

3. The sensor of claim 1, wherein the insulating layer conformally coats the field dielectric.

4. The sensor of claim 1, wherein the insulating layer conformally coats the field dielectric, and an exposed surface of the non-conductive carrier.

5. The sensor of claim 1, further comprising:
   circuit components, wherein the dielectric layer, the sensing layer, and the circuit components are operable to sense pH of a conductive fluid when the sensing layer is exposed to the conductive fluid.

6. The sensor of claim 1, further comprising:
   a first electrode;
   a second electrode;
   a first via formed in the conductive substrate, the first via electrically connecting a source diffusion region to the first electrode; and
   a second via formed in the conductive substrate, the second via electrically connecting a drain diffusion region to the second electrode, wherein, when the sensor is operable, the sensing layer functions as a gate, and the conductive substrate functions as a channel.

7. The sensor of claim 6, further comprising:
   a layer of silicon dioxide formed between the non-conductive carrier and the second surface of the conductive substrate, the layer of silicon dioxide overlaying the first electrode and the second electrode.

8. The sensor of claim 1, wherein the conductive substrate is a silicon substrate.

9. The sensor of claim 1, wherein the conductive substrate is a p doped silicon substrate.

10. The sensor of claim 1, wherein the dielectric layer and sensing layer sense pH when exposed to a conductive fluid.

11. A method of forming a sensor that is immune to stray currents, comprising
    coating a first surface of a conductive substrate with a dielectric layer;
    coating a portion of the dielectric layer with a sensing layer;
    segmenting the conductive substrate, wherein sidewalls are exposed; and
    conformally forming an insulating layer over at least the sidewalls, wherein a first surface of the sensing layer is uncoated by the insulating layer.

12. The method of claim 11, further comprising:
    positioning the conductive substrate on a non-conductive carrier.

13. The method of claim 11, further comprising:
    positioning the conductive substrate on a non-conductive carrier prior to conformally forming the insulating layer over at least the sidewalls, wherein the insulating layer overlays a portion of a surface of the non-conductive carrier.

14. The method of claim 11, further comprising;
    etching a portion of the dielectric layer, wherein coating the portion of the dielectric layer with the sensing layer includes:
    coating the etched portion of the dielectric layer with the sensing layer.

15. The method of claim 11, further comprising:
    forming a first electrode in a non-conductive carrier;
    forming a second electrode in the non-conductive carrier;
    forming a first via in the conductive substrate;
    forming a second via in the conductive substrate; and
    positioning the conductive substrate on a non-conductive carrier.

16. The method of claim 15, further comprising:
    forming an insulating layer between the non-conductive carrier and a second surface of the conductive substrate, the insulating layer overlaying the first electrode and the second electrode;
    forming a first conductive material in the insulating layer; and
    forming a second conductive material in the insulating layer.

17. The method of claim 15, further comprising:
    forming a layer of silicon dioxide between the non-conductive carrier and a second surface of the conductive substrate, the layer of silicon dioxide overlaying the first electrode and the second electrode;
    forming a first conductive pad in the layer of silicon dioxide; and
    forming a second conductive pad in the layer of silicon dioxide.

18. The method of claim 15, wherein forming the first via in the conductive substrate comprises:
    etching a first cavity in the conductive substrate; and
    coating an inner surface of the first cavity with a metal or a metal alloy, and wherein forming the second via in the conductive substrate comprises:
    etching a second cavity in the conductive substrate; and
    coating an inner surface of the second cavity with the metal or the metal alloy.

19. A pH sensor comprising:
    a non-conductive carrier;
    a first electrode inlaid in the non-conductive carrier;
    a second electrode inlaid in the non-conductive carrier;
    a conductive substrate having a first surface, a second surface, and side-walls, the conductive substrate overlaying at least a portion of the non-conductive carrier;
    a dielectric layer overlaying the first surface of the conductive substrate, the dielectric layer including a gate dielectric having a first thickness and a field dielectric having a second thickness;
    a sensing layer overlaying a first surface of the gate dielectric;

an insulating layer conformally coating at least the sidewalls of the conductive substrate, wherein a first surface of the sensing layer is uncoated by the insulating layer;

a first via formed in the conductive substrate, the first via electrically connecting a source diffusion to the first electrode; and a second via formed in the conductive substrate, the second via electrically connecting a drain diffusion to the second electrode, wherein, when the pH sensor is operable, the sensing layer functions as a gate, and the conductive substrate functions a channel.

20. The pH sensor of claim 19, further comprising:

a layer of oxide formed between the non-conductive carrier and the second surface of the conductive substrate overlaying the first electrode and the second electrode;

a first conductive pad extending through the layer of oxide; and a second conductive pad extending through the layer of oxide.

* * * * *